United States Patent
Wang et al.

(10) Patent No.: US 10,786,598 B2
(45) Date of Patent: Sep. 29, 2020

(54) COLLAGEN-SILK FIBROIN CO-ASSEMBLED SPONGE MATERIAL, CO-ASSEMBLED ARTIFICIAL SKIN AND PREPARATION METHOD THEREOF

(71) Applicant: ASIA BIOMATERIALS (WUHAN) CO., LTD., Wuhan (CN)

(72) Inventors: Jianglin Wang, Wuhan (CN); Hongchuan Ye, Wuhan (CN); Zehui Liu, Wuhan (CN); Yingying Du, Wuhan (CN)

(73) Assignee: ASIA BIOMATERIALS (WUHAN) CO., LTD., Wuhan (CN)

( * ) Notice: Subject to any disclaimer, the term of this patent is extended or adjusted under 35 U.S.C. 154(b) by 11 days.

(21) Appl. No.: 16/005,704

(22) Filed: Jun. 12, 2018

(65) Prior Publication Data
US 2019/0282730 A1    Sep. 19, 2019

(30) Foreign Application Priority Data
Mar. 19, 2018    (CN) .......................... 2018 1 0225731

(51) Int. Cl.
| A61L 27/24 | (2006.01) |
| A61L 27/34 | (2006.01) |
| A61L 27/36 | (2006.01) |
| A61L 27/56 | (2006.01) |
| A61L 27/60 | (2006.01) |

(52) U.S. Cl.
CPC .............. *A61L 27/24* (2013.01); *A61L 27/34* (2013.01); *A61L 27/3604* (2013.01); *A61L 27/56* (2013.01); *A61L 27/60* (2013.01); *A61L 2430/40* (2013.01)

(58) Field of Classification Search
CPC ..................................................... A61L 27/24
See application file for complete search history.

(56) References Cited

U.S. PATENT DOCUMENTS

2016/0206778 A1*    7/2016  Park .......................... A61F 2/08

FOREIGN PATENT DOCUMENTS

| CN | 103961749 A | 8/2014 |
| CN | 107050521 A | 8/2017 |

* cited by examiner

*Primary Examiner* — Matthew W Schall
(74) *Attorney, Agent, or Firm* — Platinum Intellectual Property LLP (57) ABSTRACT

The present invention relates to a collagen-silk fibroin co-assembled sponge material, co-assembled artificial skin and a preparation method thereof. The collagen-silk fibroin co-assembled sponge material has an ordered porous spatial structure and is prepared from a collagen-silk fibroin co-assembled product obtained by co-assembly of collagen and silk fibroin. The co-assembled artificial skin comprises a collagen-silk fibroin co-assembled sponge dermis and an epidermis. The dermis of the co-assembled artificial skin provided in the present invention is similar to the natural extracellular matrix in composition and structure. This kind of ordered novel structure can induce ordered arrangement and regeneration of cells, thereby promoting wound healing, reducing scar formation and achieving good biocompatibility.

13 Claims, 3 Drawing Sheets

COLLAGEN-SILK FIBROIN CO-ASSEMBLED SPONGE MATERIAL, CO-ASSEMBLED ARTIFICIAL SKIN AND PREPARATION METHOD THEREOF

RELATED APPLICATIONS

This application is a Non-provisional Application under 35 USC 111(a), which claims Chinese Patent Application Serial No. 201810225731.4, filed Mar. 19, 2018, the disclosure of all of which are hereby incorporated by reference in their entirety.

TECHNICAL FIELD

This present invention is directed to a collagen-silk fibroin co-assembled sponge material, co-assembled artificial skin and a preparation method thereof, belonging to the field of biomedical materials.

BACKGROUND OF THE INVENTION

Skin is one of the largest and most important human organs and has the functions of respiration, body fluid loss protection, biological barrier and the like. The large-area skin defect caused by severe burn, deep scald, severe trauma, infection, ulcer or the like is a major clinical problem. The current common methods include autologous skin transplantation, allogeneic skin transplantation and heterogeneous skin transplantation, but they often have the shortcomings of short supply, immunological rejection, susceptibility to spread diseases and the like. The above mentioned shortcomings can be effectively overcome by developing the artificial skin which is similar to human normal skin in structure and function using the principles and technique of biomaterials and tissue engineering. The artificial skin acts as a replacement of the damaged skin, and plays a role in protecting the wound surface and promoting wound healing. Obviously, the preparation materials for the artificial skin should have the characteristics of safe and wide source, low immunogenicity, good biocompatibility, good mechanical properties, induction of autologous skin regeneration, controlled degradation and the like. The ideal artificial skin should be able to imitate the structure and function of human normal skin, the ideal artificial skin should have basic structures such as an epidermis, a dermis and the like, and can provide a suitable spatial environment for adhesion, proliferation, differentiation and migration of stem cells, fibroblasts and the like related to skin regeneration, and can promote wound healing.

Collagen is one of the main components of the extracellular matrix, the collagen has the properties of good biocompatibility, biodegradability, low immunogenicity, low cytotoxicity, cell growth promotion and the like, and has been widely applied to the development of artificial skin. Pelnac® is commercially available collagen-based bilayer artificial skin, in which its epidermis consists of a silicone film, and has the functions of protecting the wound surface, preventing moisture loss, preventing bacterial infection and the like; the dermis consists of single collagen sponge, and the porous collagen sponge can induce cell aggregation, promote the growth of capillaries and play a role in promoting wound healing. However, the mechanical properties, degradation cycle and spatial structure of the single collagen sponge dermis need to be improved. In Chinese invention patent No. CN 103961749 A "Method for Preparing Collagen/Silicone Film Bilayer Scaffold", the epidermis is a silicone film, and the dermis is single collagen sponge made by different cross-linking methods. Although the mechanical properties and degradation cycle of the dermis have been improved to a certain extent, the spatial structure of its sponge needs to be improved. Because it is difficult to meet the comprehensive requirements of artificial skin based on a single collagen material, the extensive research currently is to prepare collagen-based composite materials by cross-linking or composite collagen with other synthetic polymers or natural polymers, so as to solve some problems of the single collagen material in application. The dermis of commercialized artificial skin Integra® consists of sponge prepared by covalent cross-linking of collagen and 6-chondroitin sulfate, and the epidermis is a silicone film. Although the mechanical properties of the composite porous scaffold of the dermis have been slightly improved, the artificial skin has the shortcomings of difficulty in controlling the degradation cycle, irregular porous structure and the like due to the great differences in structure, properties and the like of the collagen and the 6-chondroitin sulfate. In Chinese invention patent No. CN 107050521 A "Bilayer Collagen Dermis Scaffold and Preparation Method Thereof", the epidermis is a silicone film, the dermis is a collagen-chondroitin sulfate composite scaffold, and the dermis also has the shortcoming of disordered porous structure.

As one of the earliest natural materials used by human beings, silk is a natural polymer material with excellent properties, and in recent years, silk has been widely used in biotechnology, medicine, fine chemicals and many other aspects, such as surgical sutures, painting, cosmetics, slow release of medicaments, immobilization of separation membranes and bioactive substances, fabrication of biosensors and the like. Silk fibroin with characteristics of abundant source and low cost accounts for about 70%-80% of silk, has good biocompatibility, cell adhesion and biodegradability, and it does not have irritation or side effect of toxic, and at the same time, the silk fibroin has good mechanical properties, which can solve the problems of insufficient mechanical properties of collagen, too short degradation cycle and the like, that makes the silk fibroin an excellent natural biological material.

SUMMARY OF THE INVENTION

The present invention aims at overcoming the shortcomings in the prior art, and provides a collagen-silk fibroin co-assembled sponge material prepared by a co-assembly technique, co-assembled artificial skin and a preparation method thereof. The dermis of the co-assembled artificial skin provided in the present invention is similar to the natural extracellular matrix in composition and structure. This kind of ordered novel structure can induce ordered arrangement and regeneration of cells, thereby promoting wound healing, reducing scar formation and achieving good biocompatibility.

In order to achieve the above-stated object, the present invention adopts the following technical solution:

Provide a collagen-silk fibroin co-assembled sponge material, which has an ordered porous spatial structure and is prepared from a collagen-silk fibroin co-assembled product obtained by co-assembly of collagen and silk fibroin, and the collagen-silk fibroin co-assembled product has a stable secondary structure.

According to the above solution, the collagen-silk fibroin co-assembled sponge has a pore size of 50~500 μm and a porosity of more than 75%.

According to the above solution, the collagen-silk fibroin co-assembled sponge material is prepared from the collagen-silk fibroin co-assembled product by performing freeze-drying, crosslinking and freeze-drying process; the collagen-silk fibroin co-assembled product is obtained by mixing a collagen solution and a silk fibroin solution with the molar ratio of collagen:silk fibroin is 1:1, performing uniform mechanical stirring and co-assembly process.

Preferably, the collagen solution has a concentration of 1~10 μmol/L; and the silk fibroin solution has a concentration of 1~20 μmol/L.

According to the above solution, the co-assembly process is performed at a temperature of 0~37° C. and a humidity of 40%~80% for 12~48 h.

Preferably, the collagen is type I atelocollagen; and the silk fibroin is *Bombyx mori* silk fibroin.

Provide a co-assembled artificial skin, including a dermis and an epidermis, the dermis is the above-mentioned collagen-silk fibroin co-assembled sponge.

Preferably, the epidermis is a silicone film.

Provide a preparation method of the co-assembled artificial skin, including the following steps:

(1) preparing a collagen solution and a silk fibroin solution;

(2) mixing the collagen solution and the silk fibroin solution with the molar ratio of collagen:silk fibroin is 1:1, performing uniform mechanical stirring and co-assembly process to obtain a collagen-silk fibroin co-assembled product, and then obtaining co-assembled collagen-silk fibroin sponge by performing freeze-drying, crosslinking and freeze-drying process;

(3) coating the co-assembled collagen-silk fibroin sponge with a layer of silicone film, and curing at room temperature to obtain co-assembled artificial skin.

Preferably, the uniform mechanical stirring process is performed at a revolving speed of 1~400 rpm and a temperature of 0~37° C. for 0.5~24 h.

Preferably, the co-assembly process is performed at a temperature of 0~37° C. and a humidity of 40%~80% for 12~48 h.

Preferably, the first freeze-drying process in step (2) includes: performing gradient temperature reduction freezing process at four temperatures of 0° C., −20° C., −40° C. and −80° C. in sequence, the freezing time is 12~48 h at each temperature; and then performing freeze-drying on the obtained frozen contents at a temperature of −40~−120° C. and a pressure of 1~50 Pa for 24~72 h.

Preferably, in step (2), the crosslinking process is wet-heat crosslinking or EDC/NHS system crosslinking or glutaraldehyde system crosslinking; the wet-heat crosslinking process is performed at a temperature of 37~100° C. and a humidity of 50~80% for 1~120 h; the EDC/NHS system crosslinking process is performed in 5~50 mmol/L EDC, 1.5~32.5 mmol/L NHS and 95% ethanol at a temperature of 0~37° C. for 1~48 h; and the glutaraldehyde system crosslinking process is performed in 0.1~0.5% glutaraldehyde at a temperature of 0~37° C. for 1~48 h.

Preferably, in step (2), washing with pure water is performed after crosslinking process and then the second freeze-drying process is performed, wherein the freeze-drying process includes: performing gradient temperature reduction freezing process at four temperatures of 0° C., −20° C., −40° C. and −80° C. in sequence, the freezing time is 12~48 h at each temperature; and then performing freeze-drying on the obtained frozen contents at a temperature of −40~−120° C. and a pressure of 1~50 Pa for 24~72 h.

Preferably, in step (3), silicone film is glued on the co-assembled collagen-silk fibroin sponge with a glue gun, then coated uniformly with a polytetrafluoroethylene scraper and cured at room temperature to obtain co-assembled artificial skin.

The present invention adopts collagen and silk fibroin as raw materials, a novel co-assembled product with a stable secondary structure is obtained through a co-assembly technique at first, then ordered and structurally-matched collagen-silk fibroin co-assembled sponge is obtained by performing freeze-drying, crosslinking and freeze-drying process, and the obtained co-assembled collagen-silk fibroin sponge material can be used for preparing artificial skin. Specifically, the collagen-silk fibroin sponge material is used as a dermis and then coated with an epidermis to obtain the co-assembled artificial skin.

The dermis of the co-assembled artificial skin provided in the present invention is similar to the natural extracellular matrix in composition and structure, the pore size is suitable for implantation of stem cells, fibroblasts and the like related to skin wound healing, and the porous and ordered structure can provide an ordered and regular spatial configuration for the adhesion, growth, proliferation and differentiation of cells related to wound healing of skin, and can induce ordered arrangement and regeneration of cells, thereby promoting wound healing and reducing scar formation. The epidermis of the co-assembled artificial skin provided in the present invention has the effects of protecting the wound surface, preventing infection, preventing the loss of body fluid and facilitating suture fixation of the artificial skin. Thus, the co-assembled artificial skin provided in the present invention not only has good biocompatibility, mechanical properties and controllable degradability, but also can induce ordered arrangement and regeneration of cells, thereby reducing scar formation, improving the healing quality, promoting wound healing, and effectively filling the defects of the existing artificial skin scaffold materials, such as disordered spatial structure, poor mechanical properties, short degradation cycle, regeneration of scars and the like.

As mentioned above, the present invention has the following significant advantages:

(1) The collagen-silk fibroin co-assembled sponge prepared by the co-assembly technique in the present invention has an ordered porous spatial structure, and this kind of ordered and structurally-matched novel material not only has good biocompatibility, mechanical properties and controllable degradability, but also can induce ordered arrangement and regeneration of cells, reduce scar formation, improve the healing quality and promote wound healing as the dermis of artificial skin.

(2) The collagen-silk fibroin co-assembled sponge material provided in the present invention is adjustable in mechanical properties, degradation rate and pore size. Relatively speaking, higher concentrations of the collagen solution and the silk fibroin solution, higher co-assembly temperature and longer co-assembly time are beneficial to improving the mechanical properties of the dermis, reducing the degradation rate and reducing the pore size. Thus, the present invention can meet different clinical requirements by controlling the concentrations of the collagen solution and the silk fibroin solution and the co-assembly process condition.

(3) The co-assembled artificial skin prepared in the present invention preferably uses type I atelocollagen to avoid the problems of immunological rejection, foreign body reaction, virus infection and the like of the artificial skin in application.

(4) The epidermis in the co-assembled artificial skin prepared in the present invention preferably uses a silicone film, wherein the silicone has strong adhesion, can be firmly bonded with the collagen-silk fibroin co-assembled sponge to achieve a certain supporting effect on local tissues and is conducive to suture fixation of the artificial skin. At the same time, it has the effects of protecting the wound surface, preventing infection and preventing the loss of body fluid, and its good semi-permeability provides a relatively moist environment for wound repair and accelerates wound healing.

(5) The collagen-silk fibroin co-assembled sponge material is prepared using collagen and silk fibroin as raw materials, wherein sources of the raw materials are safe and sufficient. The shape, thickness, spatial structure, mechanical properties, degradation rate and the like of the artificial skin prepared based on the collagen-silk fibroin co-assembled sponge material are controllable. At the same time, the preparation method is simple and mature in process, and facilitates industrialized production.

The technical solutions of the present invention will be further specifically described below in combination with the accompanying drawings and specific embodiments.

DETAILED DESCRIPTION OF THE EMBODIMENTS

The embodiments of the present invention will be described below through specific examples. Those skilled in the art could easily understand other advantages and effects of the present invention from the disclosure in this specification. The present invention can also be implemented or applied through other different specific embodiments. The details in this specification can also be modified or changed based on different viewpoints and applications without departing from the spirit of the present invention.

Example 1

(1) Type I atelocollagen is dissolved in 0.5 mol/L acetic acid solution to prepare a solution of 2.5 μmol/L collagen. Freeze-dried *Bombyx mori* silk fibroin powder is dissolved in a $CaCl_2/CH_3CH_2OH/H_2O$ solution (molar ratio of 1:2:8), then the solution is dialyzed in pure water using a dialysis bag (molecular weight cutoff:3500) to prepare a solution of 2.5 μmol/L silk fibroin.

(2) Mix the 2.5 μmol/L collagen solution and the 2.5 μmol/L silk fibroin solution in equal volume, perform mechanical stirring for 8 h at a revolving speed of 200 rpm and a temperature of 0° C., then perform co-assembly for 48 h at a temperature of 0° C. and a humidity of 40% (collagen-silk fibroin co-assembled product), freeze the mixed solution after co-assembly at four temperatures of 0° C., −20° C., −40° C. and −80° C. for 12 h in sequence, and then perform drying for 48 h at −80° C. under 1 Pa. Perform wet-heat crosslinking on the obtained freeze-dried product at a temperature of 37° C. and a humidity of 80% for 90 min, wash with pure water multiple times after crosslinking, freeze for 12 h at the four temperatures of 0° C., −20° C., −40° C. and −80° C. in sequence, and then perform drying for 48 h at −80° C. under 1 Pa to obtain co-assembled collagen-silk fibroin sponge.

(3) Coat the co-assembled collagen-silk fibroin sponge with a silicone film, and cure at room temperature to obtain co-assembled artificial skin. The dermis of the co-assembled artificial skin has an ordered porous spatial structure with a pore size of 200~300 μm and a porosity of more than 80%.

Figure 1:
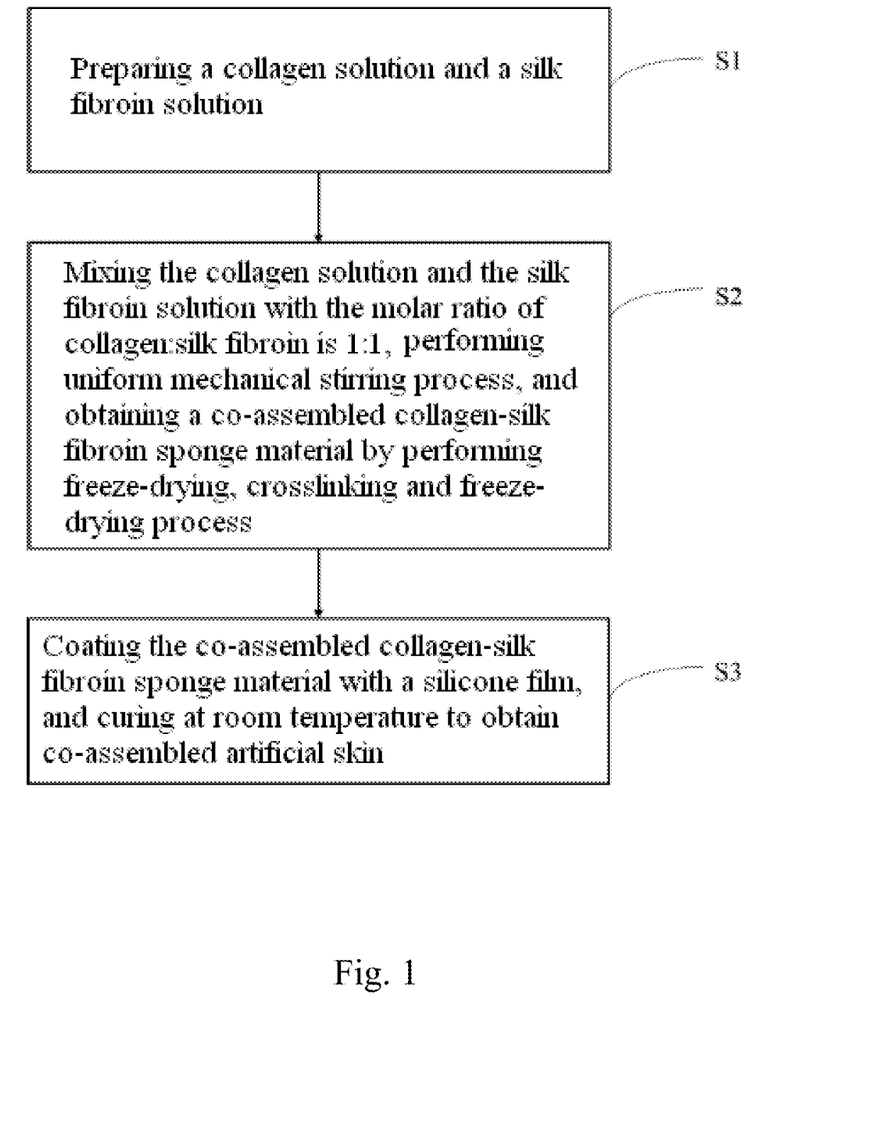
FIG. 1 is a flow diagram of a preparation process of a collagen-silk fibroin co-assembled sponge material and co-assembled artificial skin in the present invention.

The process flow diagram of the preparation method of the co-assembled artificial skin is shown in FIG. 1.

The circular dichroism spectra of the collagen-silk fibroin co-assembled product obtained by co-assembly in the above mentioned step (2), a collagen self-assembled product and a silk fibroin self-assembled product in aqueous solutions is shown in FIG. 2A.

The circular dichroism spectra of a collagen-silk fibroin composite product in an aqueous solution is shown in FIG. 2B.

The collagen self-assembled product and the silk fibroin self-assembled product are obtained by preparing 2.5 μmol/L collagen solution and silk fibroin solution respectively, performing mechanical stirring at a revolving speed of 200 rpm and a temperature of 0° C. for 8 h respectively, and then performing separate self-assembly at a temperature of 0° C. and a humidity of 40% for 48 h to obtain the collagen self-assembled product and the silk fibroin self-assembled product (in the aqueous solution) respectively.

The collagen-silk fibroin composite product is obtained by preparing 2.5 μmol/L collagen solution and silk fibroin solution respectively, mixing them in equal volume, and performing mechanical stirring at a revolving speed of 200 rpm and a temperature of 0° C. for 8 h to obtain the collagen-silk fibroin composite product (in the aqueous solution).

Figure 2:
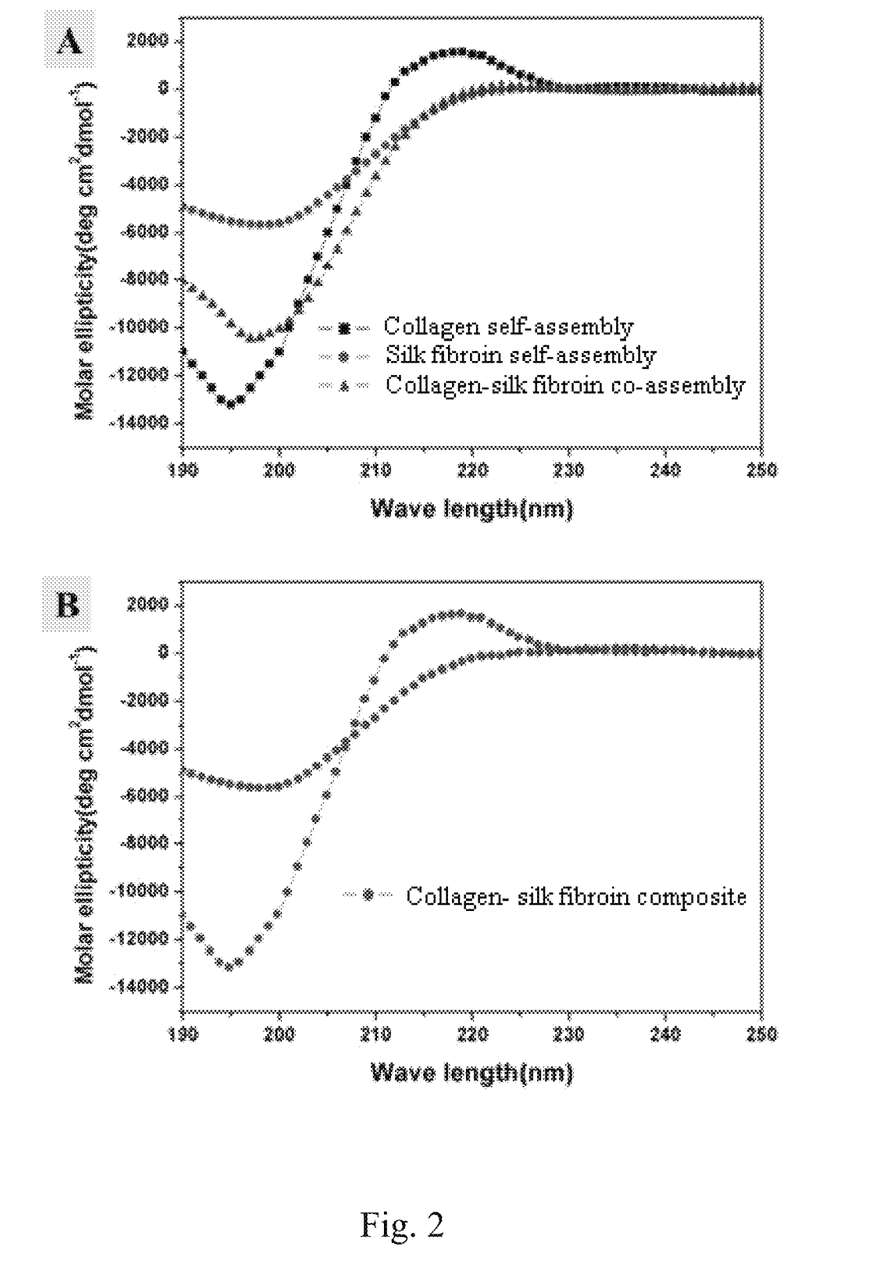
FIG. 2 shows the circular dichroism spectra of products obtained by collagen self-assembly, silk fibroin self-assembly, collagen-silk fibroin composite and collagen-silk fibroin co-assembly in aqueous solutions. The circular dichroism spectra of the collagen-silk fibroin co-assembled product of the present invention, the collagen self-assembled product and the silk fibroin self-assembled product in the aqueous solutions is shown in FIG. 2A; and the circular dichroism spectra of the collagen-silk fibroin composite product in the aqueous solution is shown in FIG. 2B.

FIG. 2 shows that the collagen self-assembled product has a typical triple-helical structure characterized by a negative peak at 195 nm and a strong positive peak at 220 nm; and the silk fibroin self-assembled product mainly has an random coil structure characterized by a strong negative peak at 195-200 nm; and the result of the collagen-silk fibroin composite product only shows the feature structures of the collagen self-assembled product and the silk fibroin self-assembled product, but does not show any new structure. It indicates that collagen-silk fibroin composite is only the mechanical mixing and only general mixing of the two components.

The distribution of the secondary structure in the collagen-silk fibroin co-assembled product system is α-helix 0%, β-sheet 44.2%, β-turn 15.3% and Random 40.5%. The whole α-helix structure in the system is transformed towards β-sheet and β-turn, and the whole system is transformed to a stable state, indicating the formation of a new secondary structure. This indicates that a co-assembly phenomenon occurs when collagen interacts with silk fibroin. Well adapted spatial coordination and structural fit are generated due to the influence of weak interactions of hydrogen bonds, electrostatic interaction, Van der Waals' force and the like to form the new secondary structure. This new co-assembled product with an ordered secondary structure and a regular spatial configuration is also a prerequisite for the preparation of ordered and structurally-matched novel materials.

A scanning electron microscope graph of the collagen-silk fibroin co-assembled sponge material obtained in the above mentioned step (2) is shown in FIG. 3D. The collagen self-assembled sponge material is shown in FIG. 3A, the silk fibroin self-assembled sponge material is shown in FIG. 3B, and the collagen-silk fibroin composite sponge material is shown in FIG. 3C.

1) The self-assembled sponge is obtained as follows: prepare 2.5 μmol/L collagen solution and silk fibroin solution respectively, perform mechanical stirring at a revolving speed of 200 rpm and a temperature of 0° C. for 8 h respectively, and then perform separate self-assembly at a temperature of 0° C. and a humidity of 40% for 48 h respectively. Freeze the solutions after self-assembly at four temperatures of 0° C., −20° C., −40° C. and −80° C. for 12 h in sequence, and then perform drying for 48 h at −80° C. under 1 Pa. Perform wet-heat crosslinking on the obtained freeze-dried product at a temperature of 37° C. and a humidity of 80% for 90 min, wash with pure water multiple times after crosslinking, freeze for 12 h at the four temperatures of 0° C., −20° C., −40° C. and −80° C. in sequence, and then perform drying for 48 h at −80° C. under 1 Pa to obtain collagen self-assembled sponge and silk fibroin self-assembled sponge respectively.

2) The collagen-silk fibroin composite sponge is obtained: in embodiment 1, after the collagen solution and the silk fibroin solution are mixed uniformly, the collagen-silk fibroin composite sponge is obtained directly by performing freeze-drying, crosslinking and freeze-drying process without co-assembly.

Figure 3:
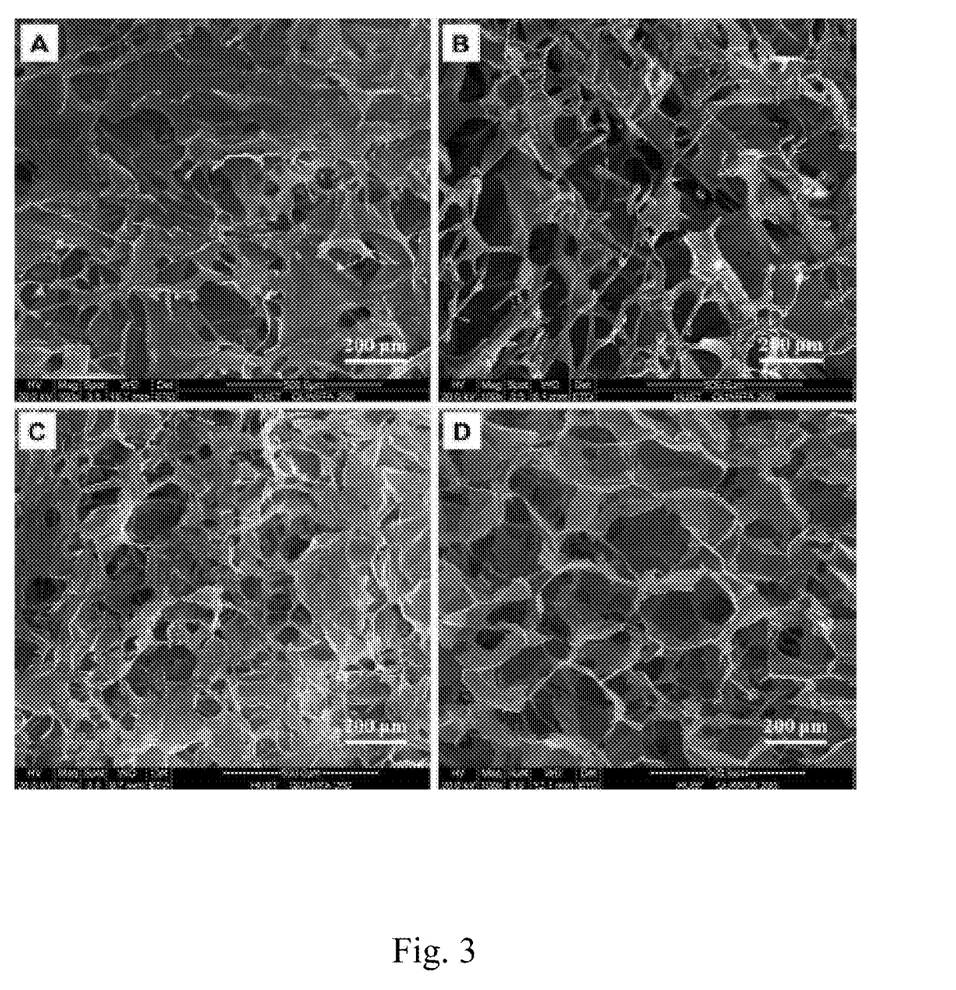
FIG. 3 shows the scanning electron microscopy graphs of a collagen-silk fibroin co-assembled sponge material prepared in Example 1, a collagen self-assembled sponge material, a silk fibroin self-assembled sponge material and a collagen-silk fibroin composite sponge material, in which A is a collagen self-assembled sponge material, B is a silk fibroin self-assembled sponge material, C is a common collagen-silk fibroin composite sponge material, and D is a collagen-silk fibroin co-assembled sponge material.

FIG. 3 shows: compared with the collagen self-assembled sponge material, the silk fibroin self-assembled sponge material and the collagen-silk fibroin composite sponge material, the collagen-silk fibroin co-assembled sponge material has the outstanding advantages of porosity, high porosity, large internal surface area, uniform pore size distribution, regular spatial structure and the like. The electron microscopy detection result also has very significant consistency and mutual verification with the circular dichroism detection result in FIG. 2.

In summary, the dermis of the co-assembled artificial skin of the present invention is closer to the natural extracellular matrix in composition and structure. Thus, an ordered and regular spatial configuration can be provided for the adhesion, growth, proliferation and differentiation of cells related to skin regeneration, and ordered arrangement and regeneration of cells can be induced to promote wound healing and reduce scar formation.

Example 2

Type I atelocollagen is dissolved in 0.5 mol/L acetic acid solution to prepare a solution of 5.0 μmol/L collagen. Freeze-dried *Bombyx mori* silk fibroin powder is dissolved in a $CaCl_2/CH_3CH_2OH/H_2O$ solution (molar ratio of 1:2:8), then the solution is dialyzed in pure water using a dialysis bag (molecular weight cutoff:3500) to prepare a solution of 5.0 μmol/L silk fibroin.

(2) Mix the 5.0 μmol/L collagen solution and the 5.0 μmol/L silk fibroin solution in equal volume, perform mechanical stirring for 4 h at a revolving speed of 150 rpm and a temperature of 20° C., then perform co-assembly for 24 h at a temperature of 20° C. and a humidity of 60%, freeze the mixed solution after co-assembly at four temperatures of 0° C., −20° C., −40° C. and −80° C. for 24 h in sequence, and then perform drying for 60 h at −80° C. under 1 Pa. Perform wet-heat crosslinking on the freeze-dried product at a temperature of 37° C. and a humidity of 80% for 90 min, wash with pure water multiple times after crosslinking, freeze for 12 h at the four temperatures of 0° C., −20° C., −40° C. and −80° C. in sequence, and then perform drying for 60 h at −80° C. under 1 Pa to obtain co-assembled collagen-silk fibroin sponge.

(3) Coat the co-assembled collagen-silk fibroin sponge with a silicone film, and cure at room temperature to obtain co-assembled artificial skin. The dermis of the obtained co-assembled artificial skin has an ordered porous spatial structure with a pore size of 120-200 μm and a porosity of more than 80%.

Example 3

(1) Type I atelocollagen is dissolved in 0.5 mol/L acetic acid solution to prepare a solution of 10.0 μmol/L collagen. Freeze-dried *Bombyx mori* silk fibroin powder is dissolved in a $CaCl_2/CH_3CH_2OH/H_2O$ solution (molar ratio of 1:2:8), then the solution is dialyzed in pure water using a dialysis bag (molecular weight cutoff:3500) to prepare a solution of 10.0 μmol/L silk fibroin.

(2) Mix the 10.0 μmol/L collagen solution and the 10.0 μmol/L silk fibroin solution in equal volume, perform mechanical stirring for 1 h at a revolving speed of 100 rpm and a temperature of 37° C., then perform co-assembly for 12 h at a temperature of 37° C. and a humidity of 80%, freeze the mixed solution after co-assembly at four temperatures of 0° C., −20° C., −40° C. and −80° C. for 36 h in sequence, and then perform drying for 72 h at −80° C. under 1 Pa. Perform wet-heat crosslinking on the obtained freeze-dried product at a temperature of 37° C. and a humidity of 80% for 90 min, wash with pure water multiple times after crosslinking, freeze for 36 h at the four temperatures of 0° C., −20° C., −40° C. and −80° C. in sequence, and then perform drying for 72 h at −80° C. under 1 Pa to obtain co-assembled collagen-silk fibroin sponge.

(3) Coat the co-assembled collagen-silk fibroin sponge with a silicone film, and cure at room temperature to obtain co-assembled artificial skin. The dermis of the obtained co-assembled artificial skin has an ordered porous spatial structure with a pore size of 50-150 μm and a porosity of more than 80%.

Example 4

(1) Type I atelocollagen is dissolved in 0.5 mol/L acetic acid solution to prepare a solution of 2.5 μmol/L collagen. Freeze-dried *Bombyx mori* silk fibroin powder is dissolved in a $CaCl_2/CH_3CH_2OH/H_2O$ solution (molar ratio of 1:2:8), then the solution is dialyzed in pure water using a dialysis bag (molecular weight cutoff:3500) to prepare a solution of 2.5 μmol/L silk fibroin.

(2) Mix the 2.5 μmol/L collagen solution and the 2.5 μmol/L silk fibroin solution in equal volume, perform mechanical stirring for 8 h at a revolving speed of 200 rpm and a temperature of 0° C., then perform co-assembly for 48 h at a temperature of 0° C. and a humidity of 40%, freeze the mixed solution after co-assembly at four temperatures of 0° C., −20° C., −40° C. and −80° C. for 12 h in sequence, and then perform drying for 48 h at −80° C. under 1 Pa. Perform crosslinking on the obtained freeze-dried product in 0.1% (w/w) glutaraldehyde at 4° C. for 24 h, wash with pure water multiple times after crosslinking, freeze for 12 h at the four temperatures of 0° C., −20° C., −40° C. and −80° C. in sequence, and then perform drying for 48 h at −80° C. under 1 Pa to obtain co-assembled collagen-silk fibroin sponge.

(3) Coat the co-assembled collagen-silk fibroin sponge with a silicone film, and cure at room temperature to obtain co-assembled artificial skin. The dermis of the co-assembled artificial skin has an ordered porous spatial structure with a pore size of 200-300 μm and a porosity of more than 80%.

Example 5

(1) Type I atelocollagen is dissolved in 0.5 mol/L acetic acid solution to prepare a solution of 5.0 μmol/L collagen. Freeze-dried *Bombyx mori* silk fibroin powder is dissolved in a $CaCl_2/CH_3CH_2OH/H_2O$ solution (molar ratio of 1:2:8), then the solution is dialyzed in pure water using a dialysis bag (molecular weight cutoff:3500) to prepare a solution of 5.0 μmol/L silk fibroin.

(2) Mix the 5.0 μmol/L collagen solution and the 5.0 μmol/L silk fibroin solution in equal volume, perform mechanical stirring for 4 h at a revolving speed of 150 rpm and a temperature of 20° C., then perform co-assembly for 24 h at a temperature of 20° C. and a humidity of 60%, freeze the mixed solution after co-assembly at four temperatures of 0° C., −20° C., −40° C. and −80° C. for 24 h in sequence, and then perform drying for 60 h at −80° C. under 1 Pa. Perform cross linking on the obtained freeze-dried product in 0.1% (w/w) glutaraldehyde at 4° C. for 24 h, wash with pure water multiple times after crosslinking, freeze for 12 h at the four temperatures of 0° C., −20° C., −40° C. and −80° C. in sequence, and then perform drying for 60 h at −80° C. under 1 Pa to obtain co-assembled collagen-silk fibroin sponge.

(3) Coat the co-assembled collagen-silk fibroin sponge with a silicone film, and cure at room temperature to obtain co-assembled artificial skin. The dermis of the obtained co-assembled artificial skin has an ordered porous spatial structure with a pore size of 120-200 μm and a porosity of more than 80%.

Example 6

(1) Type I atelocollagen is dissolved in 0.5 mol/L acetic acid solution to prepare a solution of 10.0 μmol/L collagen. Freeze-dried *Bombyx mori* silk fibroin powder is dissolved in a $CaCl_2/CH_3CH_2OH/H_2O$ solution (molar ratio of 1:2:8), then the solution is dialyzed in pure water using a dialysis bag (molecular weight cutoff:3500) to prepare a solution of 10.0 μmol/L silk fibroin.

(2) Mix the 10.0 μmol/L collagen solution and the 10.0 μmol/L silk fibroin solution in equal volume, perform mechanical stirring for 1 h at a revolving speed of 100 rpm and a temperature of 37° C., then perform co-assembly for 12 h at a temperature of 37° C. and a humidity of 80%, freeze the mixed solution after co-assembly at four temperatures of 0° C., −20° C., −40° C. and −80° C. for 36 h in sequence, and then perform drying for 72 h at −80° C. under 1 Pa. Perform crosslinking on the obtained freeze-dried product in 0.1% (w/w) glutaraldehyde at 4° C. for 24 h, wash with pure water multiple times after crosslinking, freeze for 36 h at the four temperatures of 0° C., −20° C., −40° C. and −80° C. in sequence, and then perform drying for 72 h at −80° C. under 1 Pa to obtain co-assembled collagen-silk fibroin sponge.

(3) Coat the co-assembled collagen-silk fibroin sponge with a silicone film, and cure at room temperature to obtain co-assembled artificial skin. The dermis of the obtained co-assembled artificial skin has an ordered porous spatial structure with a pore size of 50-150 μm and a porosity of more than 80%.

Example 7

(1) Type I atelocollagen is dissolved in 0.5 mol/L acetic acid solution to prepare a solution of 2.5 μmol/L collagen. Freeze-dried *Bombyx mori* silk fibroin powder is dissolved in a $CaCl_2/CH_3CH_2OH/H_2O$ solution (molar ratio of 1:2:8), then the solution is dialyzed in pure water using a dialysis bag (molecular weight cutoff:3500) to prepare a solution of 2.5 μmol/L silk fibroin.

(2) Mix the 2.5 μmol/L collagen solution and the 2.5 μmol/L silk fibroin solution in equal volume, perform mechanical stirring for 8 h at a revolving speed of 200 rpm and a temperature of 0° C., then perform co-assembly for 48 h at a temperature of 0° C. and a humidity of 40%, freeze the mixed solution after co-assembly at four temperatures of 0° C., −20° C., −40° C. and −80° C. for 12 h in sequence, and then perform drying for 48 h at −80° C. under 1 Pa. Perform crosslinking on the obtained freeze-dried product in 25 mmol/L EDC, 16 mmol/L NHS and 95% ethanol at 20° C. for 12 h, wash with pure water multiple times after crosslinking, freeze for 12 h at the four temperatures of 0° C., −20° C., −40° C. and −80° C. in sequence, and then perform drying for 48 h at −80° C. under 1 Pa to obtain co-assembled collagen-silk fibroin sponge.

(3) Coat the co-assembled collagen-silk fibroin sponge with a silicone film, and cure at room temperature to obtain co-assembled artificial skin. The dermis of the co-assembled artificial skin has an ordered porous spatial structure with a pore size of 200-300 μm and a porosity of more than 80%.

Example 8

(1) Type I atelocollagen is dissolved in 0.5 mol/L acetic acid solution to prepare a solution of 5.0 μmol/L collagen. Freeze-dried *Bombyx mori* silk fibroin powder is dissolved in a $CaCl_2/CH_3CH_2OH/H_2O$ solution (molar ratio of 1:2:8), then the solution is dialyzed in pure water using a dialysis bag (molecular weight cutoff:3500) to prepare a solution of 5.0 μmol/L silk fibroin.

(2) Mix the 5.0 μmol/L collagen solution and the 5.0 μmol/L silk fibroin solution in equal volume, perform mechanical stirring for 4 h at a revolving speed of 150 rpm and a temperature of 20° C., then perform co-assembly for 24 h at a temperature of 20° C. and a humidity of 60%, freeze the mixed solution after co-assembly at four temperatures of 0° C., −20° C., −40° C. and −80° C. for 24 h in sequence, and then perform drying for 60 h at −80° C. under 1 Pa. Perform crosslinking on the obtained freeze-dried product in 25 mmol/L EDC, 16 mmol/L NHS and 95% ethanol at 20° C. for 12 h, wash with pure water multiple times after crosslinking, freeze for 12 h at the four temperatures of 0° C., −20° C., −40° C. and −80° C. in sequence, and then perform drying for 60 h at −80° C. under 1 Pa to obtain co-assembled collagen-silk fibroin sponge.

(3) Coat the co-assembled collagen-silk fibroin sponge with a silicone film, and cure at room temperature to obtain co-assembled artificial skin. The dermis of the obtained co-assembled artificial skin has an ordered porous spatial structure with a pore size of 120-200 μm and a porosity of more than 80%.

Example 9

(1) Type I atelocollagen is dissolved in 0.5 mol/L acetic acid solution to prepare a solution of 10.0 μmol/L collagen. Freeze-dried *Bombyx mori* silk fibroin powder is dissolved in a $CaCl_2/CH_3CH_2OH/H_2O$ solution (molar ratio of 1:2:8), then the solution is dialyzed in pure water using a dialysis bag (molecular weight cutoff:3500) to prepare a solution of 10.0 μmol/L silk fibroin.

(2) Mix the 10.0 μmol/L collagen solution and the 10.0 μmol/L silk fibroin solution in equal volume, perform mechanical stirring for 1 h at a revolving speed of 100 rpm and a temperature of 37° C., then perform co-assembly for 12 h at a temperature of 37° C. and a humidity of 80%, freeze the mixed solution after co-assembly at four temperatures of 0° C., −20° C., −40° C. and −80° C. for 36 h in sequence, and then perform drying for 72 h at −80° C. under 1 Pa. Perform crosslinking on the obtained freeze-dried product in 25 mmol/L EDC, 16 mmol/L NHS and 95% ethanol at 20° C. for 12 h, wash with pure water multiple times after crosslinking, freeze for 36 h at the four temperatures of 0° C., −20° C., −40° C. and −80° C. in sequence, and then perform drying for 72 h at −80° C. under 1 Pa to obtain co-assembled collagen-silk fibroin sponge.

(3) Coat the co-assembled collagen-silk fibroin sponge with a silicone film, and cure at room temperature to obtain co-assembled artificial skin. The dermis of the obtained co-assembled artificial skin has an ordered porous spatial structure with a pore size of 50-150 μm and a porosity of more than 80%.

The invention claimed is:
1. A collagen-silk fibroin co-assembled homogenous sponge material, wherein the collagen-silk fibroin co-assembled sponge material has an ordered porous spatial structure and is prepared from a collagen-silk fibroin co-assembled product obtained by co-assembly of collagen and silk fibroin.

2. The collagen-silk fibroin co-assembled homogenous sponge material according to claim 1, wherein the collagen is type I atelocollagen; and the silk fibroin is *Bombyx mori* silk fibroin.

3. The collagen-silk fibroin co-assembled homogenous sponge material according to claim 1, wherein the collagen-silk fibroin co-assembled sponge has a pore size of 50~500 μm and a porosity of more than 75%.

4. The collagen-silk fibroin co-assembled homogenous sponge material according to claim 1, wherein the collagen-silk fibroin co-assembled homogenous sponge material is prepared from the collagen-silk fibroin co-assembled product by performing freeze-drying, crosslinking and freeze-drying process; and the collagen-silk fibroin co-assembled product has a stable secondary structure, and it is obtained by mixing a collagen solution and a silk fibroin solution with the molar ratio of collagen:silk fibroin is 1:1, performing uniform mechanical stirring and co-assembly process.

5. The collagen-silk fibroin co-assembled homogenous sponge material according to claim 1, wherein the co-assembly process is performed at a temperature of 0~37° C. and a humidity of 40%~80% for 12~48 h.

6. A co-assembled artificial skin, comprising a dermis and an epidermis, wherein the dermis is made of the collagen-silk fibroin co-assembled homogenous sponge material of claim 1.

7. The co-assembled artificial skin according to claim 6, wherein the epidermis is a silicone film.

8. The collagen-silk fibroin co-assembled homogenous sponge material of claim 1, wherein the collagen-silk fibroin co-assembled homogenous sponge material is prepared by:
(1) preparing a collagen solution and a silk fibroin solution;
(2) mixing the collagen solution and the silk fibroin solution with the molar ratio of collagen:silk fibroin is 1:1, performing uniform mechanical stirring and co-assembly process to obtain a collagen-silk fibroin co-assembled product, and then obtaining co-assembled collagen-silk fibroin sponge material by performing freeze-drying, crosslinking and freeze-drying process.

9. The collagen-silk fibroin co-assembled homogenous sponge material of claim 8, wherein, in the step (2), the uniform mechanical stirring process is performed at a revolving speed of 1~400 rpm and a temperature of 0~37° C. for 0.5~24 h;
the first freeze-drying process in the step (2) is: performing gradient temperature reduction freezing process at four temperatures of 0° C., −20° C., −40° C. and −80° C. in sequence, the freezing time is 12~48 h at each temperature; and then performing freeze-drying on the obtained frozen contents at a temperature of −40~−120° C. and a pressure of 1~50 Pa for 24~72 h;
the crosslinking process is wet-heat crosslinking or EDC/NHS system crosslinking or glutaraldehyde system crosslinking; the wet-heat crosslinking is performed at a temperature of 37~100° C. and a humidity of 50~80% for 1~120 h; the EDC/NHS system crosslinking is performed in 5~50 mmol/L EDC, 1.5~32.5 mmol/L NHS and 95% ethanol at a temperature of 0~37° C. for 1~48 h; the glutaraldehyde system crosslinking is performed in 0.1~0.5% glutaraldehyde at a temperature of 0~37° C. for 1~48 h;
washing with pure water is performed after crosslinking and then the second freeze-drying is performed, the freeze-drying includes: performing gradient temperature reduction freezing at four temperatures of 0° C., −20° C., −40° C. and −80° C. in sequence, the freezing time being 12~48 h at each temperature; and then performing freeze-drying on the obtained frozen contents at a temperature of −40~−120° C. and a pressure of 1~50 Pa for 24~72 h.

10. The co-assembled artificial skin of claim 7, wherein the co-assembled artificial skin is prepared by:
(1) preparing a collagen solution and a silk fibroin solution;
(2) mixing the collagen solution and the silk fibroin solution with the molar ratio of collagen:silk fibroin is 1:1, performing uniform mechanical stirring and co-assembly process to obtain a collagen-silk fibroin co-assembled product, and then obtaining co-assembled collagen-silk fibroin sponge by performing freeze-drying, crosslinking and freeze-drying process, and
(3) coating the co-assembled collagen-silk fibroin sponge with a layer of silicone film, and curing at room temperature to obtain co-assembled artificial skin.

11. The co-assembled artificial skin of claim 10, wherein, in the step (2), the uniform mechanical stirring process is performed at a revolving speed of 1~400 rpm and a temperature of 0~37° C. for 0.5~24 h;

the first freeze-drying process in the step (2) is: performing gradient temperature reduction freezing process at four temperatures of 0° C., −20° C., −40° C. and −80° C. in sequence, the freezing time is 12~48 h at each temperature; and then performing freeze-drying on the obtained frozen contents at a temperature of −40~−120° C. and a pressure of 1~50 Pa for 24~72 h;

the crosslinking process is wet-heat crosslinking or EDC/NHS system crosslinking or glutaraldehyde system crosslinking; the wet-heat crosslinking is performed at a temperature of 37~100° C. and a humidity of 50~80% for 1~120 h; the EDC/NHS system crosslinking is performed in 5~50 mmol/L EDC, 1.5~32.5 mmol/L NHS and 95% ethanol at a temperature of 0~37° C. for 1~48 h; the glutaraldehyde system crosslinking is performed in 0.1~0.5% glutaraldehyde at a temperature of 0~37° C. for 1~48 h;

washing with pure water is performed after crosslinking and then the second freeze-drying is performed, the freeze-drying includes: performing gradient temperature reduction freezing at four temperatures of 0° C., −20° C., −40° C. and −80° C. in sequence, the freezing time being 12~48 h at each temperature; and then performing freeze-drying on the obtained frozen contents at a temperature of −40~−120° C. and a pressure of 1~50 Pa for 24~72 h.

12. The co-assembled artificial skin of claim 10, wherein, in the step (3), silicone film is glued on the co-assembled collagen-silk fibroin sponge with a glue gun, then coated uniformly with a polytetrafluoroethylene scraper and cured at room temperature to obtain co-assembled artificial skin.

13. A collagen-silk fibroin co-assembled homogenous sponge material, wherein the collagen-silk fibroin co-assembled sponge material has an ordered porous spatial structure and is prepared from a collagen-silk fibroin co-assembled product obtained by co-assembly of collagen and silk fibroin, the ordered porous spatial structure with a pore size of 120-200 μm and a porosity of more than 80%.

* * * * *